(12) United States Patent
Tillett et al.

(10) Patent No.: US 11,534,211 B2
(45) Date of Patent: Dec. 27, 2022

(54) SYSTEMS AND METHODS FOR PERFORMING LATERAL-ACCESS SPINE SURGERY

(71) Applicant: Mobius Imaging, LLC, Shirley, MA (US)

(72) Inventors: Jason Tillett, Shirley, MA (US); Scott Coppen, Amesbury, MA (US); Gordon Row, Groton, MA (US)

(73) Assignee: Mobius Imaging LLC, Shirley, MA (US)

( * ) Notice: Subject to any disclaimer, the term of this patent is extended or adjusted under 35 U.S.C. 154(b) by 343 days.

(21) Appl. No.: 16/605,743

(22) PCT Filed: Oct. 4, 2018

(86) PCT No.: PCT/US2018/054395
§ 371 (c)(1),
(2) Date: Oct. 16, 2019

(87) PCT Pub. No.: WO2019/070997
PCT Pub. Date: Apr. 11, 2019

(65) Prior Publication Data
US 2020/0146731 A1    May 14, 2020

Related U.S. Application Data

(60) Provisional application No. 62/568,267, filed on Oct. 4, 2017.

(51) Int. Cl.
*A61B 17/70* (2006.01)
*A61B 34/30* (2016.01)
(Continued)

(52) U.S. Cl.
CPC ...... *A61B 17/7074* (2013.01); *A61B 17/0206* (2013.01); *A61B 34/20* (2016.02);
(Continued)

(58) Field of Classification Search
CPC ............ A61B 17/7074; A61B 17/0206; A61B 17/0293; A61B 34/20; A61B 34/30;
(Continued)

(56) References Cited

U.S. PATENT DOCUMENTS

| 5,799,055 A | 8/1998 | Peshkin et al. |
| 5,921,992 A | 7/1999 | Costales et al. |

(Continued)

FOREIGN PATENT DOCUMENTS

| CN | 201422918 Y | 3/2010 |
| CN | 201542641 U | 8/2010 |

(Continued)

OTHER PUBLICATIONS

English language abstract and machine-assisted English translation for CN 201422918 extracted from espacenet.com database on Jan. 9, 2020, 7 pages.

(Continued)

*Primary Examiner* — Tan-Uyen T Ho
*Assistant Examiner* — Bridget E. Rabaglia
(74) *Attorney, Agent, or Firm* — Howard & Howard Attorneys PLLC

(57) ABSTRACT

A retractor apparatus for a surgical robotic system includes a frame defining a central open region, a connecting member that connects the frame to a robotic arm, a plurality of coupling mechanisms for attaching a set of retractor blades within the central open region of the frame such that blades define a working channel interior of the blades, and a plurality of actuators extending between the frame and each of the coupling mechanisms and configured to move the blades with respect to the frame to vary a dimension of the working channel. Further embodiments include a surgical robotic system that includes a robotic arm and a retractor apparatus attached to the robotic arm, and methods for (Continued)

performing a robot-assisted surgical procedure using a retractor apparatus attached to a robotic arm.

18 Claims, 10 Drawing Sheets

(51) Int. Cl.
   *A61B 17/02* (2006.01)
   *A61B 34/20* (2016.01)
   *A61B 34/10* (2016.01)
   *A61B 17/00* (2006.01)

(52) U.S. Cl.
   CPC .... *A61B 34/30* (2016.02); *A61B 2017/00022* (2013.01); *A61B 2017/00115* (2013.01); *A61B 2034/107* (2016.02); *A61B 2034/2055* (2016.02); *A61B 2034/2065* (2016.02)

(58) Field of Classification Search
   CPC ........... A61B 2017/00022; A61B 2017/00115; A61B 2034/107; A61B 2034/2065
   See application file for complete search history.

(56) References Cited

U.S. PATENT DOCUMENTS

| | | | |
|---|---|---|---|
| 6,149,592 A * | 11/2000 | Yanof | A61B 90/36 606/130 |
| 6,236,875 B1 | 5/2001 | Bucholz et al. | |
| 6,275,725 B1 | 8/2001 | Cosman | |
| 6,468,207 B1 * | 10/2002 | Fowler, Jr. | A61B 17/0206 600/217 |
| 6,533,455 B2 | 3/2003 | Graumann et al. | |
| 6,772,002 B2 | 8/2004 | Schmidt et al. | |
| 6,785,572 B2 | 8/2004 | Yanof et al. | |
| 7,194,120 B2 | 3/2007 | Wicker et al. | |
| 7,251,522 B2 | 7/2007 | Essenreiter et al. | |
| 7,587,235 B2 | 9/2009 | Wist et al. | |
| 7,699,877 B2 | 4/2010 | Davison | |
| 7,722,530 B2 | 5/2010 | Davison | |
| 7,799,036 B2 | 9/2010 | Davison et al. | |
| 7,946,982 B2 * | 5/2011 | Hamada | A61B 1/32 600/233 |
| 8,016,835 B2 | 9/2011 | Birkmeyer et al. | |
| 8,046,054 B2 | 10/2011 | Kim et al. | |
| 8,118,488 B2 | 2/2012 | Gregerson | |
| 8,126,114 B2 | 2/2012 | Naylor et al. | |
| 8,394,144 B2 | 3/2013 | Zehavi et al. | |
| 8,454,583 B2 | 6/2013 | Perez-Cruet et al. | |
| 8,457,790 B2 | 6/2013 | Blondel et al. | |
| 8,509,503 B2 | 8/2013 | Nahum et al. | |
| 8,761,337 B2 | 6/2014 | Naylor et al. | |
| 8,795,188 B2 | 8/2014 | Maschke | |
| 8,821,394 B2 * | 9/2014 | Hawkins | A61B 17/0293 600/214 |
| 8,968,363 B2 * | 3/2015 | Weiman | A61B 17/02 606/231 |
| 8,974,460 B2 | 3/2015 | De la Fuente Klein et al. | |
| 8,992,425 B2 * | 3/2015 | Karpowicz | A61B 17/0218 600/233 |
| 9,125,680 B2 | 9/2015 | Kostrzewski et al. | |
| 9,237,861 B2 | 1/2016 | Nahum et al. | |
| 9,259,282 B2 | 2/2016 | Azizian et al. | |
| 9,283,048 B2 | 3/2016 | Kostrzewski et al. | |
| 9,308,050 B2 | 4/2016 | Kostrzewski et al. | |
| 9,545,233 B2 | 1/2017 | Sirpad et al. | |
| 9,550,299 B2 | 1/2017 | Wolf et al. | |
| 9,579,095 B2 * | 2/2017 | Perrow | A61B 17/025 |
| 9,750,432 B2 | 9/2017 | Nahum et al. | |
| 9,833,292 B2 | 12/2017 | Kostrzewski et al. | |
| 10,004,562 B2 | 6/2018 | Kostrzewski et al. | |
| 10,039,476 B2 | 8/2018 | Nahum et al. | |
| 10,064,682 B2 | 9/2018 | Azizian et al. | |
| 10,076,385 B2 | 9/2018 | Shoham et al. | |
| 10,136,952 B2 | 11/2018 | Couture et al. | |
| 10,159,534 B2 | 12/2018 | Maillet et al. | |
| 2005/0215866 A1 | 9/2005 | Kim | |
| 2006/0224044 A1 * | 10/2006 | Marchek | A61B 17/02 600/233 |
| 2007/0156157 A1 | 7/2007 | Nahum et al. | |
| 2007/0208227 A1 | 9/2007 | Smith et al. | |
| 2007/0282171 A1 | 12/2007 | Karpowicz et al. | |
| 2008/0004632 A1 | 1/2008 | Sutherland et al. | |
| 2009/0018401 A1 | 1/2009 | Kim | |
| 2011/0098537 A1 | 4/2011 | Justis et al. | |
| 2014/0003572 A1 | 1/2014 | Gregerson et al. | |
| 2014/0005489 A1 | 1/2014 | Charles | |
| 2014/0114135 A1 | 4/2014 | Ellman | |
| 2014/0139215 A1 | 5/2014 | Gregerson et al. | |
| 2014/0249546 A1 * | 9/2014 | Shvartsberg | A61B 90/50 606/130 |
| 2014/0265182 A1 | 9/2014 | Stanton et al. | |
| 2014/0275953 A1 | 9/2014 | Gregerson et al. | |
| 2015/0088030 A1 * | 3/2015 | Taylor | A61B 5/4893 600/554 |
| 2015/0202009 A1 | 7/2015 | Nussbaumer et al. | |
| 2015/0272694 A1 * | 10/2015 | Charles | G16H 40/63 600/202 |
| 2015/0366624 A1 | 12/2015 | Kostrzewski et al. | |
| 2016/0030117 A1 | 2/2016 | Mewes | |
| 2016/0081754 A1 | 3/2016 | Kostrzewski et al. | |
| 2016/0100908 A1 | 4/2016 | Tesar | |
| 2016/0174914 A1 | 6/2016 | Lerch et al. | |
| 2016/0220320 A1 | 8/2016 | Crawford et al. | |
| 2016/0235492 A1 | 8/2016 | Morard et al. | |
| 2016/0278875 A1 | 9/2016 | Crawford et al. | |
| 2017/0071691 A1 | 3/2017 | Crawford et al. | |
| 2017/0079727 A1 | 3/2017 | Crawford et al. | |
| 2017/0172669 A1 | 6/2017 | Berkowitz et al. | |
| 2017/0231702 A1 | 8/2017 | Crawford et al. | |
| 2017/0239002 A1 | 8/2017 | Crawford et al. | |
| 2017/0239003 A1 | 8/2017 | Crawford et al. | |
| 2017/0239006 A1 | 8/2017 | Crawford et al. | |
| 2017/0245951 A1 | 8/2017 | Crawford et al. | |
| 2017/0252112 A1 | 9/2017 | Crawford et al. | |
| 2017/0258533 A1 | 9/2017 | Crawford et al. | |
| 2017/0258535 A1 * | 9/2017 | Crawford | B25J 15/0441 |
| 2017/0273679 A1 | 9/2017 | Karpowicz et al. | |
| 2017/0312039 A1 | 11/2017 | Crawford et al. | |
| 2017/0348061 A1 | 12/2017 | Joshi et al. | |
| 2017/0360513 A1 | 12/2017 | Amiot et al. | |
| 2017/0360517 A1 | 12/2017 | Crawford et al. | |
| 2018/0000546 A1 | 1/2018 | Crawford et al. | |
| 2018/0014890 A1 | 1/2018 | Stanton et al. | |
| 2018/0110573 A1 | 4/2018 | Kostrzewski | |
| 2018/0116739 A1 | 5/2018 | Gogarty et al. | |
| 2018/0116740 A1 | 5/2018 | Gogarty et al. | |
| 2018/0125597 A1 | 5/2018 | Gogarty et al. | |
| 2018/0157238 A1 | 6/2018 | Gogarty et al. | |
| 2018/0185113 A1 | 7/2018 | Gregerson et al. | |
| 2018/0207794 A1 * | 7/2018 | Sebring | B25J 9/0018 |
| 2018/0221098 A1 | 8/2018 | Forsyth et al. | |
| 2018/0235715 A1 | 8/2018 | Amiot et al. | |
| 2018/0250077 A1 | 9/2018 | Xu et al. | |
| 2018/0256259 A1 | 9/2018 | Crawford | |
| 2018/0271511 A1 | 9/2018 | Stanton | |
| 2018/0271605 A1 | 9/2018 | Kostrzewski et al. | |
| 2018/0346008 A1 | 12/2018 | Nahum et al. | |
| 2019/0000561 A1 | 1/2019 | Decker et al. | |
| 2019/0000569 A1 | 1/2019 | Crawford et al. | |
| 2019/0021795 A1 | 1/2019 | Crawford et al. | |
| 2019/0021799 A1 | 1/2019 | Crawford et al. | |
| 2019/0021800 A1 | 1/2019 | Crawford et al. | |
| 2019/0029759 A1 | 1/2019 | McDonell | |
| 2019/0029765 A1 | 1/2019 | Crawford et al. | |
| 2019/0038362 A1 | 2/2019 | Nash et al. | |
| 2019/0053859 A1 | 2/2019 | Couture et al. | |
| 2019/0069961 A1 | 3/2019 | Smith et al. | |
| 2019/0099222 A1 | 4/2019 | Nahum et al. | |
| 2019/0117313 A1 | 4/2019 | Crawford | |
| 2019/0142533 A1 | 5/2019 | Itkowitz et al. | |

(56) References Cited

U.S. PATENT DOCUMENTS

| | | |
|---|---|---|
| 2019/0239964 A1 | 8/2019 | LeBoeuf, II et al. |
| 2019/0269467 A1 | 9/2019 | Forsyth et al. |
| 2019/0274765 A1 | 9/2019 | Crawford et al. |

FOREIGN PATENT DOCUMENTS

| | | |
|---|---|---|
| CN | 101700184 B | 1/2011 |
| CN | 101579269 B | 4/2011 |
| CN | 101853333 B | 11/2012 |
| EP | 2467073 B1 | 1/2017 |
| WO | 2011060031 A1 | 5/2011 |
| WO | 2015115809 A1 | 8/2015 |
| WO | 2017036340 A1 | 3/2017 |
| WO | 2017122202 A1 | 7/2017 |
| WO | 2017134546 A2 | 8/2017 |
| WO | 2018185729 A1 | 10/2018 |

OTHER PUBLICATIONS

English language abstract and machine-assisted English translation for CN 201542641 extracted from espacenet.com database on Jan. 9, 2020, 10 pages.

English language abstract and machine-assisted English translation for CN 101700184 extracted from espacenet.com database on Jan. 9, 2020, 10 pages.

English language abstract and machine-assisted English translation for CN 101579269 extracted from espacenet.com database on Jan. 9, 2020, 8 pages.

English language abstract and machine-assisted English translation for CN 101853333 extracted from espacenet.com database on Jan. 9, 2020, 9 pages.

English language abstract and machine-assisted English translation for WO 2015/115809 extracted from espacenet.com database on Jan. 9, 2020, 8 pages.

English language abstract for WO 2017/036340 extracted from espacenet.com database on Jan. 9, 2020, 2 pages.

Pal jug, Eric et al. "The JPL Serpentine Robot: a 12 DOF System for Inspection", NASA JPL Technical Reports Server, https://trs.jpl.nasa.gov/handle/2014/29159, Jan. 1, 1995, 5 pages.

International Search Report from the Korean Intellectual Property Office in related International Application No. PCT/US2018/054395 dated Jan. 25, 2019.

Written Opinion of the International Searching Authority from the Korean Intellectual Property Office in related International Application No. PCT/US2018/054395 dated Jan. 25, 2019.

\* cited by examiner

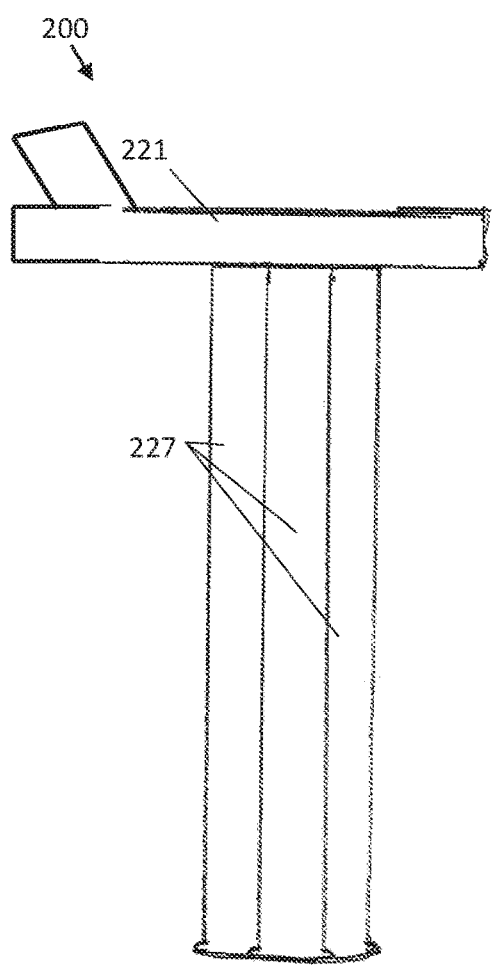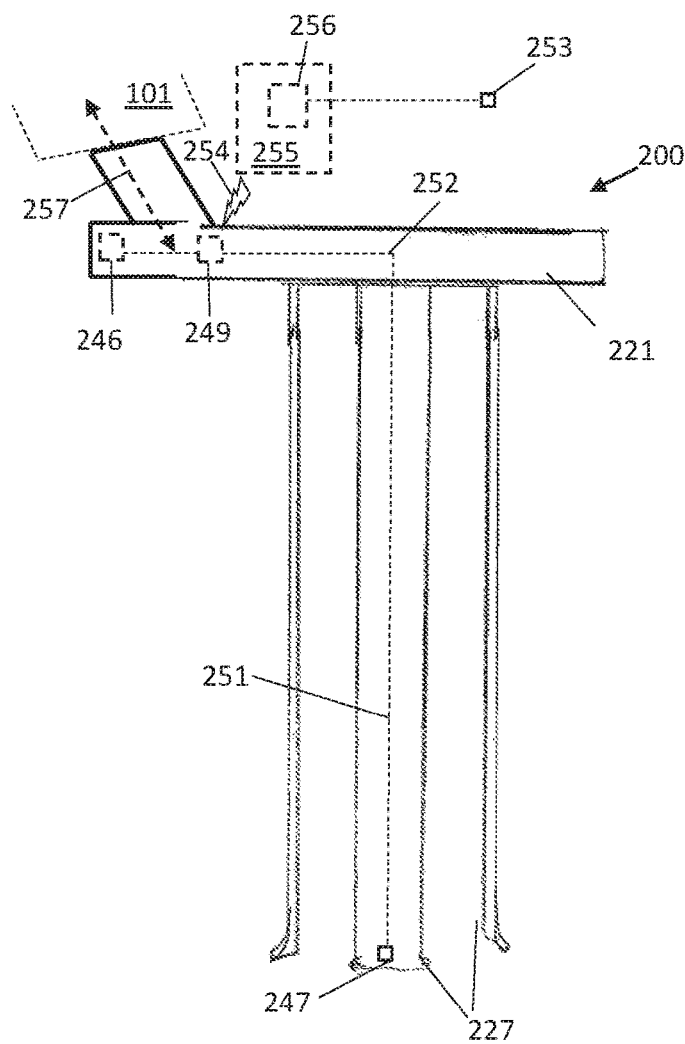
FIG. 2C
FIG. 2D

SYSTEMS AND METHODS FOR PERFORMING LATERAL-ACCESS SPINE SURGERY

RELATED APPLICATION

This application claims the benefit of priority to U.S. Provisional Application No. 62/568,267, filed Oct. 4, 2017, the entire contents of which are incorporated herein by reference.

BACKGROUND

Surgical procedures, such as minimally-invasive procedures, may require a surgeon to insert surgical tools inside the body of the patient to a particular depth to reach the target area inside the patient's body. For example, minimally invasive spinal surgical procedures have been used for stabilization of vertebral bones and spinal joints and for relieving of pressure applied to the spinal nerves. Such procedures may utilize relatively small incisions and insertion of tubular retractors and cannulas while minimizing damage to muscles and other surrounding anatomical features. Minimally invasive surgical approaches can be faster, safer and require less recovery time than conventional open surgeries. There is a continuing need for improvement to the safety and speed of surgical procedures, such as minimally-invasive surgical procedures.

SUMMARY

Various embodiments include systems and methods for performing spine surgery, including minimally invasive lateral access spine surgery. Embodiments include a retractor apparatus that may be used for robot-assisted minimally invasive lateral access spine surgery.

Embodiments include a retractor apparatus for a surgical robotic system that includes a frame defining a central open region, a connecting member that connects the frame to a robotic arm, a plurality of coupling mechanisms for attaching a set of retractor blades within the central open region of the frame such that blades define a working channel interior of the blades, and a plurality of actuators extending between the frame and each of the coupling mechanisms and configured to move the blades with respect to the frame to vary a dimension of the working channel.

Further embodiments include a surgical robotic system that includes a robotic arm and a retractor apparatus attached to the robotic arm, where the retractor apparatus includes a frame attached to the robotic arm and defining a central open region, a connecting member that connects the frame to a robotic arm, a plurality of coupling mechanisms for attaching a set of retractor blades within the central open region of the frame such that blades define a working channel interior of the blades, and a plurality of actuators extending between the frame and each of the coupling mechanisms and configured to move the blades with respect to the frame to vary a dimension of the working channel.

Further embodiments include a method for performing a robot-assisted surgical procedure that includes controlling a robotic arm having a frame of a retractor apparatus frame attached thereto to position the frame over a pre-set trajectory into the body of a patient, attaching a plurality of retractor blades to the frame such that the blades define a working channel into the body of the patient, and moving at least one retractor blade relative to the frame to vary a dimension of the working channel.

BRIEF DESCRIPTION OF THE DRAWINGS

Other features and advantages of the present invention will be apparent from the following detailed description of the invention, taken in conjunction with the accompanying drawings of which:

FIGS. 2A-2E illustrate an embodiment retractor apparatus for performing lateral-access spine surgery.

DETAILED DESCRIPTION

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

Various embodiments relate to apparatuses and methods for performing spine surgery, including minimally invasive lateral access spine surgery. Embodiments include a retractor apparatus that may be used for robot assisted minimally invasive lateral access spine surgery.

One common surgical procedure performed on the spine is an interbody fusion, which includes fusing two vertebrae together. To perform this procedure, the intervertebral space between the two vertebrae must be accessed to partially or completely remove the intervertebral disc and to insert an implant, such as a spacer or cage, that maintains the normal alignment of the spine while allowing the two vertebrae to fuse. Conventionally, the surgical space has been accessed from the posterior or anterior of the patient. However, this may require removing bony portions of the vertebral column to access the disc space. In addition, such approaches may risk damage to major vascular structures and other sensitive organs. More recently, a lateral approach has been utilized, in which the surgeon may access certain parts of the spine (e.g., the lumbar region of the spine) from the side of the patient. This may be less invasive for the patient, may result in less trauma, and can reduce operating time and recovery periods.

Figure 1:
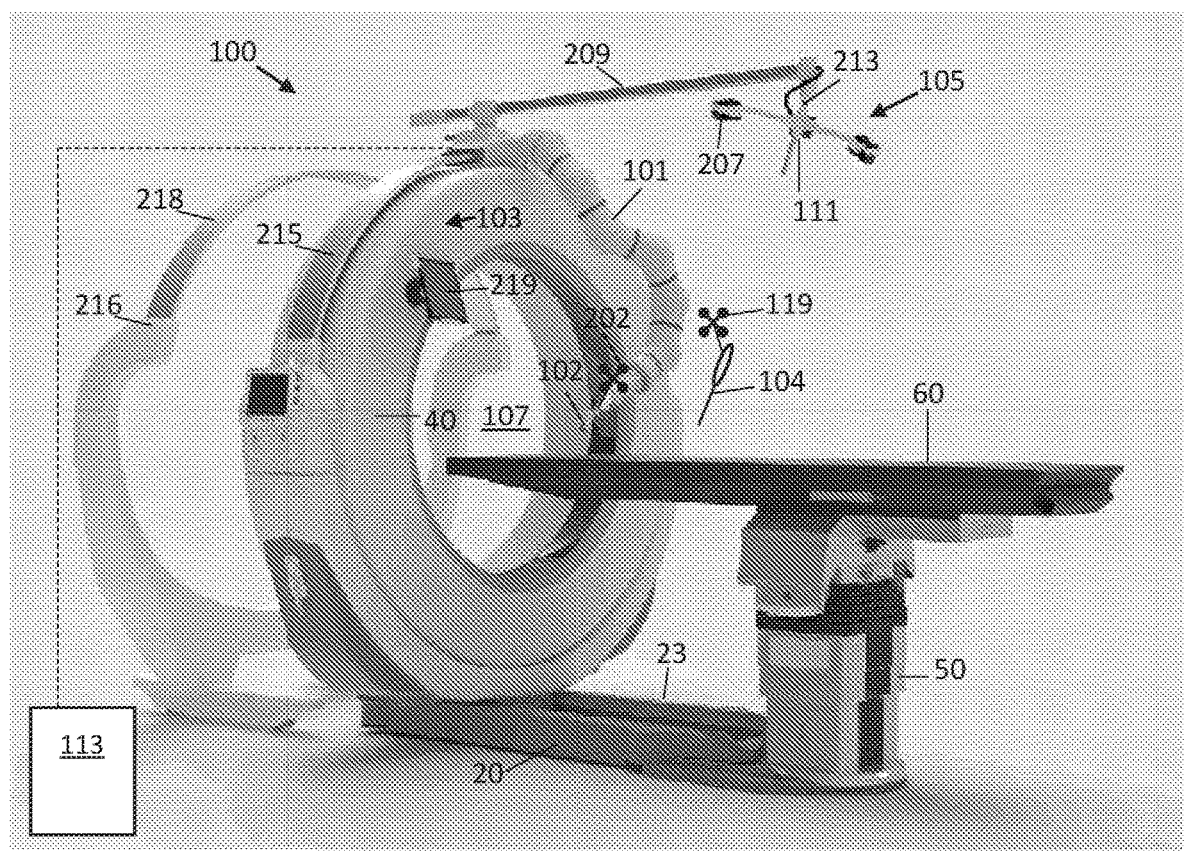
FIG. 1 illustrates a robotic-assisted surgical system according to an embodiment.

In various embodiments, a lateral-access spine procedure, such as lateral transpsoas interbody fusion, may be performed using a computer-assisted image guided surgery system. In embodiments, the system may be a surgical robotic system that may include at least one robotic arm that is configured to assist a surgeon in performing a surgical procedure. FIG. 1 illustrates a system 100 for performing computer-assisted image-guided surgery that includes an imaging device 103, a motion tracking system 105 and a robotic arm 101. The robotic arm 101 may be fixed to a support structure at one end and may have an end effector 102 located at the other end of the robotic arm 101. The robotic arm 101 may comprise a multi joint arm that includes a plurality of linkages connected by joints having actuator(s) and optional encoder(s) to enable the linkages to rotate, bend and/or translate relative to one another in response to control signals from a robot control system. The motions of the robotic arm 101 may enable the end effector 102 to be moved to various positions and/or orientations, such as various positions and/or orientations with respect to a patient (not illustrated) that may be located on a patient support 60 (e.g., surgical table). In various embodiments described in further detail below, the end effector 102 of the robotic arm 101 may include a retractor apparatus that may be used to provide a working channel to a target site within the patient.

The imaging device 103 may be used to obtain diagnostic images of a patient (not shown in FIG. 1), which may be a human or animal patient. In embodiments, the imaging device 103 may be an x-ray computed tomography (CT) imaging device. The patient may be positioned within a central bore 107 of the imaging device 103 and an x-ray source and detector may be rotated around the bore 107 to obtain x-ray image data (e.g., raw x-ray projection data) of the patient. The collected image data may be processed using a suitable processor (e.g., computer) to perform a three-dimensional reconstruction of the object. In other embodiments, the imaging device 103 may comprise one or more of an x-ray fluoroscopic imaging device, a magnetic resonance (MR) imaging device, a positron emission tomography (PET) imaging device, a single-photon emission computed tomography (SPECT), or an ultrasound imaging device. In embodiments, image data may be obtained pre-operatively (i.e., prior to performing a surgical procedure), intra-operatively (i.e., during a surgical procedure) or post-operatively (i.e., following a surgical procedure) by positioning the patient within the bore 107 of the imaging device 103. In the system 100 of FIG. 1, this may be accomplished by moving the imaging device 103 over the patient to perform a scan while the patient may remain stationary.

Examples of x-ray CT imaging devices that may be used according to various embodiments are described in, for example, U.S. Pat. No. 8,118,488, U.S. Patent Application Publication No. 2014/0139215, U.S. Patent Application Publication No. 2014/0003572, U.S. Patent Application Publication No. 2014/0265182 and U.S. Patent Application Publication No. 2014/0275953, the entire contents of all of which are incorporated herein by reference. In the embodiment shown in FIG. 1, the patient support 60 (e.g., surgical table) upon which the patient may be located is secured to the imaging device 103, such as via a column 50 which is mounted to a base 20 of the imaging device 103. A portion of the imaging device 103 (e.g., an O-shaped imaging gantry 40) which includes at least one imaging component may translate along the length of the base 20 on rails 23 to perform an imaging scan of the patient, and may translate away from the patient to an out-of-the-way position for performing a surgical procedure on the patient. It will be understood that other imaging devices may be utilized, including other mobile or fixed x-ray CT devices or a C-arm x-ray fluoroscopy device.

Further, although the imaging device 103 shown in FIG. 1 is located close to the patient within the surgical theater, the imaging device 103 may be located remote from the surgical theater, such as in another room or building (e.g., in a hospital radiology department).

The motion tracking system 105 shown in FIG. 1 includes a plurality of marker devices 119, 202 and an optical sensor device 111. Various systems and technologies exist for tracking the position (including location and/or orientation) of objects as they move within a three-dimensional space. Such systems may include a plurality of active or passive markers fixed to the object(s) to be tracked and a sensing device that detects radiation emitted by or reflected from the markers. A 3D model of the space may be constructed in software based on the signals detected by the sensing device.

The motion tracking system 105 in the embodiment of FIG. 1 includes a plurality of marker devices 119, 202 and a stereoscopic optical sensor device 111 that includes two or more cameras 207 (e.g., IR cameras). The optical sensor device 111 may include one or more radiation sources (e.g., diode ring(s)) that direct radiation (e.g., IR radiation) into the surgical field, where the radiation may be reflected by the marker devices 119, 202 and received by the cameras. The marker devices 119, 202 may each include three or more (e.g., four) reflecting spheres, which the motion tracking system 105 may use to construct a coordinate system for each of the marker devices 119, 202. A computer 113 may be coupled to the sensor device 111 and may determine the transformations between each of the marker devices 119, 202 and the cameras using, for example, triangulation techniques. A 3D model of the surgical space in a common coordinate system may be generated and continually updated using motion tracking software implemented by the computer 113. In embodiments, the computer 113 may also receive image data from the imaging device 103 and may register the image data to the common coordinate system as the motion tracking system 105 using image registration techniques as are known in the art. In embodiments, at least one reference marker device may be attached to the patient. The reference marker device may be rigidly attached to a landmark in the anatomical region of interest (e.g., clamped or otherwise attached to a bony portion of the patient's anatomy) to enable the anatomical region of interest to be continually tracked by the motion tracking system 105. Additional marker devices 119 may be attached to surgical tools or instruments 104 to enable the tools/instruments 104 to be tracked within the common coordinate system. Another marker device 202 may be rigidly attached to the robotic arm 101, such as on the end effector 102 of the robotic arm 101, to enable the position of robotic arm 101 and end effector 102 to be tracked using the motion tracking system 105. The computer 113 may also include software configured to perform a transform between the joint coordinates of the robotic arm 101 and the common coordinate system of the motion tracking system 105, which may enable the position and orientation of the end effector 102 of the robotic arm 101 to be controlled with respect to the patient.

In addition to passive marker devices described above, the motion tracking system 105 may alternately utilize active marker devices that may include radiation emitters (e.g., LEDs) that may emit radiation that is detected by an optical sensor device 111. Each active marker device or sets of active marker devices attached to a particular object may emit radiation in a pre-determined strobe pattern (e.g., with modulated pulse width, pulse rate, time slot and/or amplitude) and/or wavelength which may enable different objects to be uniquely identified and tracked by the motion tracking system 105. One or more active marker devices may be fixed relative to the patient, such as secured to the patient's skin via an adhesive membrane or mask. Additional active marker devices may be fixed to surgical tools 104 and/or to the end effector 102 of the robotic arm 101 to allow these objects to be tracked relative to the patient.

In further embodiments, the marker devices may be passive maker devices that include moiré patterns that may enable their position and orientation to be tracked in three-dimensional space using a single camera using Moiré Phase Tracking (MPT) technology. Other tracking technologies, such as computer vision systems and/or magnetic-based tracking systems, may also be utilized.

As shown in FIG. 1, the optical sensor device 111 may include a plurality of cameras 207 mounted to an arm 209 extending above the patient surgical area. The arm 209 may be mounted to or above the imaging device 103. The arm 209 may enable the sensor device 111 to pivot with respect to the arm 209 and/or the imaging device 103 (e.g., via one or more ball joints 213). The arm 209 may enable a user to adjust the position and/or orientation of the sensor device 111 to provide the cameras 207 with a clear view into the surgical field while avoiding obstructions. The arm 209 may enable the position and/or orientation of the sensor device 111 to be adjusted and then locked in place during an imaging scan or surgical procedure.

The system 100 may also include at least one display device 219 as illustrated in FIG. 1. The display device 219 may display image data of the patient's anatomy obtained by the imaging device 103. In the case of CT image data, for example, the display device 219 may display a three-dimensional volume rendering of a portion of the patient's anatomy and/or may display two-dimensional slices (e.g., axial, sagittal and/or coronal slices) through the 3D CT reconstruction dataset. The display device 219 may facilitate planning for a surgical procedure, such as by enabling a surgeon to define one or more target positions in the patient's body and/or a path or trajectory into the patient's body for inserting surgical tool(s) to reach a target position while minimizing damage to other tissue or organs of the patient. The position and/or orientation of one or more objects tracked by the motion tracking system 105 may be shown on the display 219, and may be shown overlaying the image data (e.g., using augmented reality technology). This may enable the surgeon to precisely navigate the tracked tools/implants within the patient's body in real-time. The use of tracked surgical instruments or tools in combination with pre-operative or intra-operative images of the patient's anatomy in order to guide a surgical procedure may be referred to as "image-guided surgery."

In embodiments, the display device 219 may be a handheld computing device, such as a tablet device. One or more handheld display devices 219 may be mounted to the imaging device 103, as shown in FIG. 1. In other embodiments, a handheld display device 219 may be mounted to the patient support 60 or column 50, the arm 209 that supports the optical sensing device 111 for the motion tracking system 105, or to any of the wall, ceiling or floor in the operating room, or to a separate cart. Alternately or in addition, the at least one display device 219 may be a monitor display that may be located on a mobile cart or mounted to another structure (e.g., a wall) within the surgical theater. In further embodiments, a display device 219 may be a head-mounted display that may be worn by a surgeon or other clinician.

As shown in FIG. 1, the robotic arm 101 may be fixed to the imaging device 103, such as on a support element 215 (e.g., a curved rail) that may extend concentrically over the outer surface of the O-shaped gantry 40 of the imaging device 103. In embodiments, an arm 209 to which the optical sensing device 111 is mounted may be mounted to the same or a similar support element 215 (e.g., curved rail) as the robotic arm 101. The position of the robotic arm 101 and/or the arm 209 may be adjustable along the length of the support element 215. In other embodiments, the robotic arm 101 may be secured to any other portion of the imaging device 103, such as directly mounted to the gantry 40. Alternatively, the robotic arm 101 may be mounted to the patient support 60 or column 50, to any of the wall, ceiling or floor in the operating room, or to a separate cart. FIG. 1 illustrates the robotic arm 101 mounted to a support element 215 (curved rail) that is directly attached to the imaging device 103. Alternately, the robotic arm 101 may be mounted to a mobile shuttle 216 that may moved adjacent to the imaging device 103 such that a support member 218 (e.g., a curved rail) for mounting the robotic arm 101 extends at least partially over the gantry 40 of the imaging device 103. Various exemplary systems for mounting a robotic arm 101 in a computer-assisted image guided surgery system are described in U.S. Provisional Patent Application No. 62/491,645, filed Apr. 28, 2017, the entire contents of which are incorporated by reference herein. Although a single robotic arm 101 is shown in FIG. 1, it will be understood that two or more robotic arms 101 may be utilized. Each robotic arm 101 may include an end effector 102 that may comprise or may be configured to hold an invasive surgical tool or implant.

The at least one robotic arm 101 may aid in the performance of a surgical procedure, such as a minimally-invasive spinal surgical procedure or various other types of orthopedic, neurological, cardiothoracic and general surgical procedures. In embodiments, the motion tracking system 105 may track the position of the robotic arm 101 (e.g., via marker device 202 on end effector 102 as shown in FIG. 1) within the patient coordinate system. A control loop may continuously read the tracking data and the current parameters (e.g., joint parameters) of the robotic arm 101 and may send instructions to a robotic controller to cause the robotic arm 101 to move to a desired position and orientation within the patient coordinate system.

In embodiments, a surgeon may use an image-guided surgery system as a planning tool for a surgical procedure, such as by setting trajectories within the patient for inserting surgical tools, as well as by selecting one or more target locations for a surgical intervention within the patient's body. The trajectories and/or target locations set by the surgeon may be saved (e.g., in a memory of a computer device, such as computer device 113 shown in FIG. 1) for later use during surgery. In embodiments, the surgeon may be able to select stored trajectories and/or target locations using an image guided surgery system, and the robotic arm 101 may be controlled to perform a particular movement based on the selected trajectory and/or target location. For example, the robotic arm 101 may be moved to position the end effector 102 of the robotic arm 101 into alignment with the pre-defined trajectory and/or over the pre-determined target location.

In addition to a robotic arm 101 as described above, an end effector 102 of the present embodiments may be attached to a moveable arm or boom, which may be motor-driven or manually moved. The arm may be moved to position the end effector 102 at a desired location with respect to the patient and the arm may be configured to hold its pose during a surgical intervention.

Figure 2A:
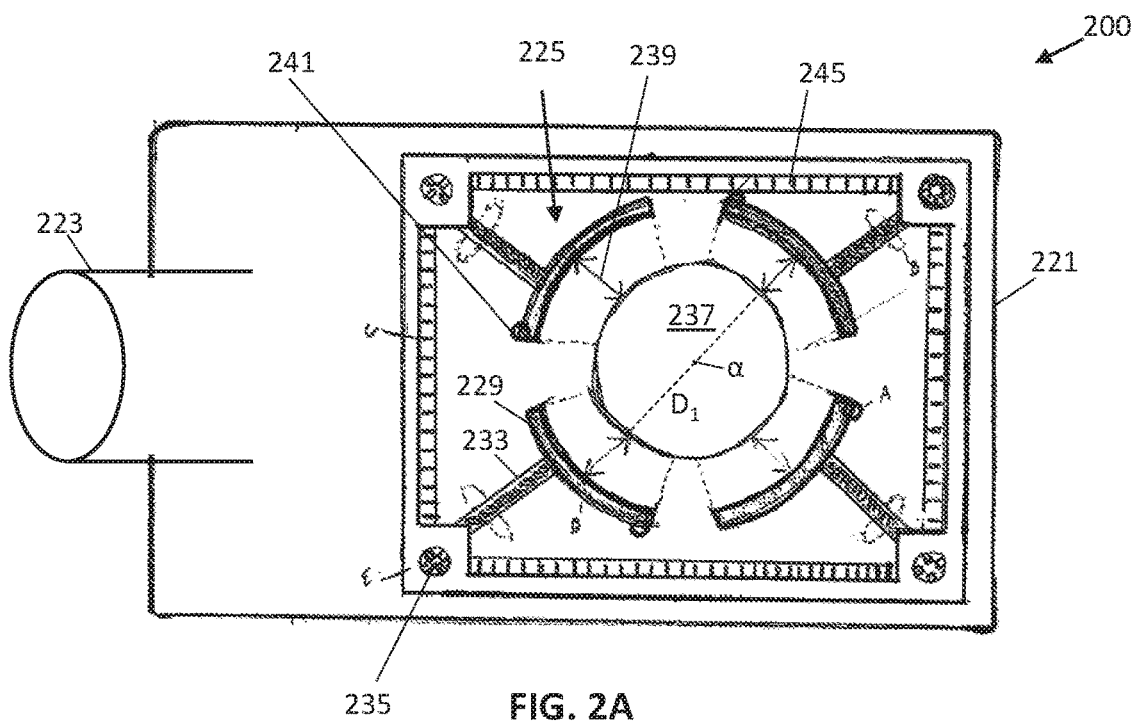

FIGS. 2A-2E schematically illustrate a retractor apparatus 200 for performing lateral-access spine surgery according to an embodiment. FIG. 2A is an overhead view of the retractor apparatus 200 and FIGS. 2B-2E are side views illustrating the retractor apparatus 200 with a plurality of retractor blades 227 mounted therein. The retractor apparatus 200 may be attached to the end of a robotic arm 101 (i.e., the retractor apparatus 200 may function as the end effector 102 of the robotic arm 101), such that the robotic arm 101 may move the retractor apparatus 200 to a desired position and/or orientation with respect to a patient. The retractor apparatus 200 includes a frame 221, which may be made from a rigid structural material. The frame 221 may optionally be made of a radiolucent material. The frame 221 may surround a central open region 225, as shown in FIG. 2A. The frame 221 in the embodiment of FIGS. 2A-2E has a rectangular shape. It will be understood that the frame 221 may have a circular or other shape. A connecting member 223 connects the frame 221 to the end of a robotic arm 101 (not illustrated in FIGS. 2A-2E). In embodiments, the robotic arm 101 may have an attachment mechanism that enables different end effectors 102, such as the retractor apparatus 200, to be attached to and removed from the end of the robotic arm 101. The retractor apparatus 200 may be fastened to the robotic arm 101 using mechanical fasteners (e.g., bolts) and/or via a quick-connect/disconnect mechanism. Alternately, the retractor apparatus 200 may be permanently mounted to the robotic arm 101.

The retractor apparatus 200 may be a sterile or sterilizable component that may not need to be draped during surgery. In some embodiments, the retractor apparatus 200 may be attached to a robotic arm 101 over a surgical drape that covers the arm 101. All or a portion of the retractor apparatus 200 may be a single-use disposable component. Alternately, all or a portion of the retractor apparatus 200 multi-use component that may be re-sterilized (e.g., autoclavable). A marker device 202 (e.g., an array of reflective spheres) may be attached to the retractor apparatus 200 and/or to the robotic arm 101 to enable the retractor apparatus 200 to be tracked by a motion tracking system 105, such as shown in FIG. 1.

The frame 221 may further include a coupling mechanism for mechanically coupling the frame 221 to a plurality of retractor blades 227 (see FIGS. 2B-2E). The retractor blades 227 may extend downwards from the central open region 225 of the frame 221. In this embodiment, the coupling mechanism comprises a plurality of guides 229 through which the retractor blades 227 may be inserted. In other embodiments, the coupling mechanism may be an attachment mechanism that engages with the side or top surface of the blades 227 to couple the blades 227 to the frame 221.

Figure 2B:
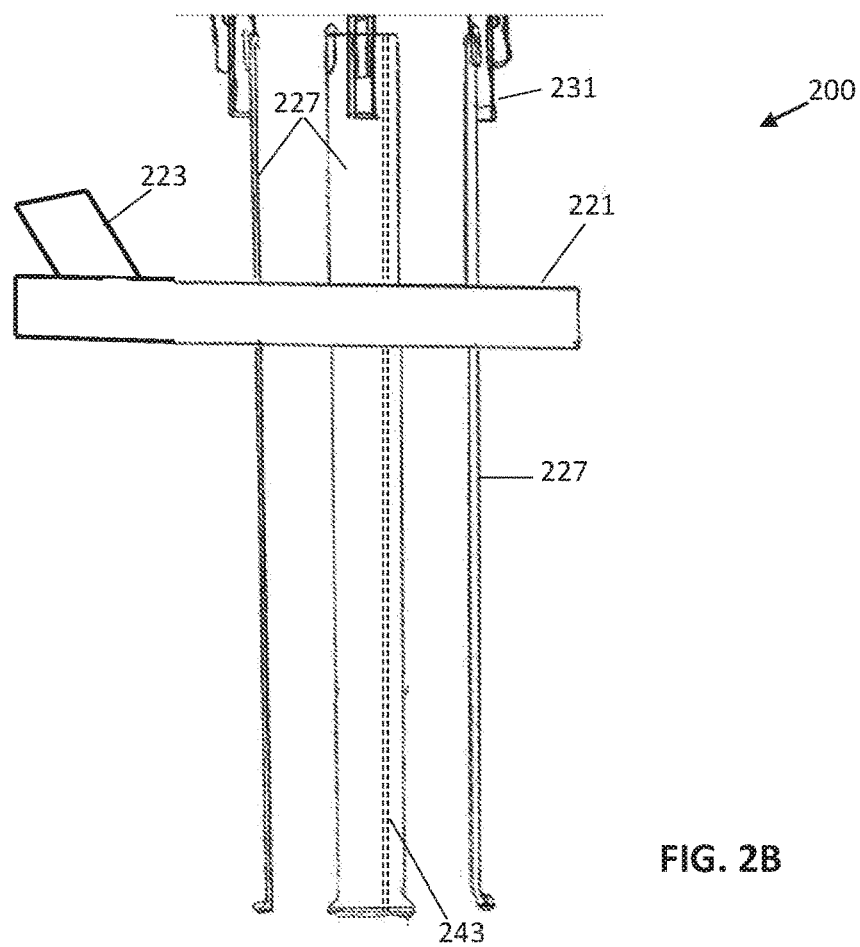

As shown in the side view of FIG. 2B, the retractor blades 227 may slide through the guides 229 to couple the blades 227 to the frame 221. The blades 227 may include clips 231 or another attachment mechanism to attach the blades 227 to the respective guides 229 when the blades 227 are fully inserted.

The retractor apparatus 200 may also include a plurality of actuators 233 for moving the retractor blades 227 radially inwards and outwards with respect to the frame 221. Each actuator 233 may include, for example, a screw, a rack-and-pinion system, or a similar apparatus that extends from the frame 221 into the central open region 225. The actuators 233 may be manually operated using a control knob, handle or other feature that enables a user to extend or retract the blades 227. As shown in FIG. 2A, the frame 221 may include a plurality of sockets 235 into which a torque device (e.g., a key, an Allen wrench, screwdriver, etc.) may be inserted such that bi-directional rotation of the torque device causes the actuator 233 to extend and retract with respect to the frame 221. In alternative embodiments, the actuators 233 may be motor-driven. For example, each actuator 233 may have an associated motor located on or within the frame 221. The motor may drive the extension and retraction of the actuator 233 and blade 227 in response to control signals received from a system controller and/or a user input device.

FIG. 2C is a side view illustrating the retractor apparatus 200 in a first configuration in which the actuators 233 are fully extended from the frame 221 into the central open region 225. The retractor blades 227 may be positioned adjacent to one another and may define a working channel 237 (see FIG. 2A) radially inward from the plurality of blades 227. FIG. 2D illustrates the retractor apparatus 200 in a second configuration in which blades 227 are retracted by the actuators 233. This is schematically illustrated in the overhead view of FIG. 2A, which shows the blades 237 retracted along the direction of arrows 239. In the first configuration, the retractor blades 227 may define a working channel 237 having a generally circular cross-section and an initial width dimension (i.e., diameter) $D_1$. The blades 237 may be retracted to a second configuration to increase the width dimension (i.e., diameter) of the working channel 237, as shown in FIG. 2A. In embodiments, each blade 227 of the retractor apparatus 200 may be moved (i.e., extended or retracted) via its associated actuator 233 independently of any movement of the other blade(s) 227.

Figure 2E:
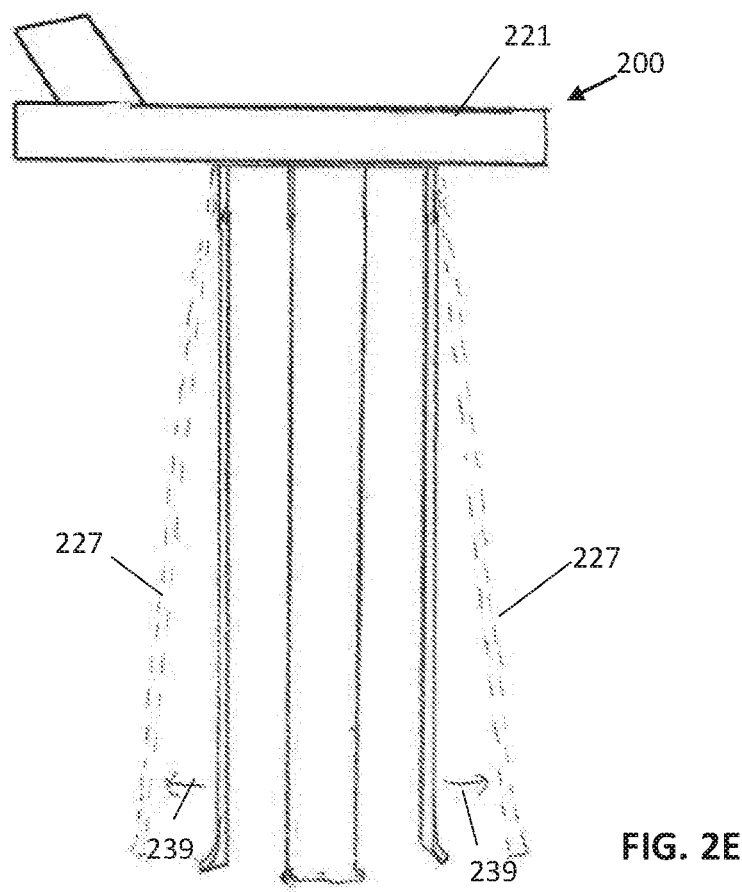

In embodiments, the blades 227 may also pivot with respect to the frame 221 of the retractor apparatus 200. This is illustrated by FIG. 2E, which shows a pair of blades 227 (depicted in phantom) that have been pivoted out with respect to the frame 221 in the direction of arrow 239. Pivoting a retractor blade 227 as illustrated may enable the width dimension of the working channel 237 to be increased proximate to the area of surgical intervention (e.g., the spine) while minimizing the size of the opening through the skin surface and peripheral tissue. In one exemplary embodiment, the pivot motion of the blades 227 may be controlled using the same input feature (e.g., control knob, handle, torque device) that is used to extend and retract the blades 227. For example, in the embodiment of FIGS. 2A-2E, turning a torque device in the socket 235 in one direction may cause the actuator 233 to retract the corresponding blade 227 towards the frame 221. After the blade 227 is fully retracted, continuing to turn the torque device in the same direction may cause the blade 227 to pivot outwards as shown in FIG. 2E. Alternately, a set of separate manual controllers (e.g., control knobs, levers, handles, torque devices, etc.) may be utilized to control the pivoting motion of the blades 227. In such a case, the pivoting motion of the blades 227 may be performed independently of the extension and retraction of the blades 227. In addition, each blade 227 may be pivoted independently of any pivoting of the other blade(s) 227. In further embodiments, the pivoting motion of the blades 227 be motor-driven, as described above.

Each retractor blade 227 may be made from a radiolucent material, such as carbon fiber. The retractor blades 227 may include electrically conductive material that forms one or more continuous electrical pathways through the blade 227. The continuous electrical pathways may be used for performing intraoperative neurophysiological monitoring (IONM), as described further below. The retractor blade(s) 227 and/or the coupling mechanism (e.g., guide(s) 229) may optionally include a port 241 or other electrical connector to enable a probe device to electrically connect to the blade 227 (e.g., for neurophysiological monitoring).

In embodiments, the retractor blades 227 may include one or more channels 243 extending through the blade 227 (shown in phantom in FIG. 2B). A channel 243 in the blade 227 may be utilized for illumination of the surgical area (e.g., by inserting an LED or other light source into the channel 243), for visualization of the surgical area (e.g., by inserting an endoscope into the channel 243) or for any other purpose (e.g., for removal of tissue/fluid via suction or other means).

A retractor apparatus 200 as described above may utilize retractor blades 227 having varying lengths. The length of the blades 227 used for a particular surgical procedure may be chosen based on the depth of the surgical site from the patient's skin surface. This depth may be determined using an image guided surgery system as described above. For example, a surgeon may use a tracked instrument to set a target trajectory and/or target location within the patient's anatomy. Based on the pre-set trajectory and/or location, the image guided surgery system may determine the appropriate size of the retractor blades 227 for insertion into the retractor apparatus 200 out of an available set of sizes for the retractor blades 227. The image guided surgery system may provide an indication to the surgeon (e.g., via a display device 219 as shown in FIG. 1) of an appropriate blade 227 size to use for the surgical procedure. In some embodiments, the image guided surgery system may control the robotic arm 101 to move the frame 221 of the retractor apparatus 200 to a pre-determined distance from the skin surface of the patient such that the tip ends of the selected retractor blades 227 are located at the proper anatomical depth within the patient.

The frame 221 of the retractor apparatus may include one or more rails 245 that may extend around the periphery of the central open region 225. The one or more rails 245 may enable tools/instruments to be clipped or clamped on to the retractor apparatus 200. For example, an illumination source or camera system (e.g., endoscope) may be attached to a desired position on a rail 245, and may optionally extend at least partially into the working channel defined by the retractor blades 227. Other tools that may be attached to a rail 245 include, for example, a suction device for removing fluids from the surgical site and/or a shim element that may be inserted into the disc space (e.g., to restore disc height and/or anchor the retractor apparatus 200 to the surgical site).

The retractor apparatus 200 of FIGS. 2A-2E includes four retractor blades 227. However, it will be understood that a retractor apparatus 200 according to various embodiments may have three blades, two blades or greater than four blades (e.g., five blades, six blades, etc.).

As discussed above, a retractor apparatus 200 may be configured to provide intraoperative neurophysiological monitoring (IONM). Use of IONM techniques may enable the surgeon to locate the proximity of tools to nerves and avoid damage or irritation to the nerves during surgery. A variety of IONM methods are known, including electromyography (EMG), including spontaneous EMG (S-EMG) and stimulus-triggered EMG (T-EMG), somatosensory evoked potentials (SSEPs) and motor evoked potentials (MEPs).

In one embodiment, IONM may be performed by electrically stimulating muscle tissue and neural structures surrounding the surgical area and measuring the evoked EMG response using sensor(s) located on or within the patient's body. A retractor apparatus 200 as described above may include at least one electrode 247 located on a retractor blade 227, as schematically shown in FIG. 2D. The electrode 247 may be configured to electrically stimulate the surrounding tissue when the blade 227 is inserted into the patient. In embodiments, each of the blades 227 of the retractor apparatus 220 may include at least one electrode 247 for stimulating the surrounding tissue. The electrode 247 in FIG. 2D is shown located at the tip end of the retractor blade 227, although it will be understood that the electrode 247 may be located at another position on the blade 227. In addition, a blade 227 may have multiple electrodes 247 located at different positions on the blade 227 for stimulating different portions of the surrounding tissue.

For performing neurophysiological monitoring, each electrode 247 may be electrically connected to a power source 246 (e.g., one or more batteries) and circuitry 249 for generating stimulation signals that may be transmitted to the electrode(s) 247 via a conductive lead 251. The conductive lead 251 may be, for example, a wire located on or within the blade 227 or a conductive trace formed on a surface of the blade 227 via printing, spray coating, etc. In embodiments, the retractor apparatus 200 may include a conductive path 252 to conduct power from the power source 246 to the blade 237. One or more sensors 253 (e.g., surface or needle electrodes) may be positioned at pre-determined locations on the patient's body corresponding to particular muscle(s) and/or neural features to measure the evoked EMG response. A processing device 255 (e.g., computer), operably coupled to the sensor(s) 253, may include a nerve detection component 256 configured to process the sensor data according to defined algorithms to determine the proximity (including distance and/or direction) of a neural structure (e.g., a nerve) to a blade 227 or a portion thereof. The nerve detection component 256 may be implemented in electronic hardware, in computer software, or in combinations of both.

The nerve detection component 256 may be coupled to a user feedback device to provide audio and/or visual feedback to the surgeon. For example, the nerve detection component 256 may be coupled to a display device 219 (see FIG. 1) configured provide feedback in the form of a visual indication on the display device 219 that a particular retractor blade 227 is proximate to a nerve and/or may be impinging on a nerve. In response to the nerve detection component 256 determining that a retractor 227 blade is too close to a nerve, the nerve detection component 256 may cause the display 219 to provide instructions to the surgeon to stop further movement of the blade 227 and/or to move the blade 227 away from the nerve. In some embodiments, a graphical depiction of one or more nerves detected using an IONM method may be overlaid with image data on the display screen of the image guided surgery system. In embodiments in which the movement of the blades 227 is motor-driven as described above, the nerve detection component 256 may be configured to send instructions to a motorized drive system of a blade to cause the motorized drive system to automatically stop movement (e.g., retraction or pivoting) of the blade 227. The nerve detection component 256 may also cause the motorized drive system to move the retractor blade 227 away from a detected nerve.

In embodiments, the nerve detection component 256 may be configured to activate the electrodes 247 on the blades 227 of the retractor apparatus 200 to stimulate the surrounding tissue. The nerve detection component 256 may be operatively coupled to circuit 249 and to the electrodes 247 on the retractor blades 227 via a wired or wireless connection. The nerve detection component 256 may be configured to control the characteristics of the stimulation signals, such as the stimulation current, the duration of the signals, and/or the frequency of the signals. In embodiments, stimulation signals may be generated in response to a user input from a user input device. In some embodiments, a plurality of stimulation signals may be generated in a pre-determined sequence or cycle (e.g., each electrode 247 of a plurality of electrodes on the retractor blades 227 may be energized sequentially).

In the embodiment shown in FIG. 2D, the power source 246 and circuitry 249 for generating stimulation signals are located on the retractor apparatus 200, and may be mounted to or within the frame 221 of the apparatus 200. The circuitry 249 may include wireless transceiver circuitry configured to provide a wireless communication link 254 between the retractor apparatus 200 and an external entity, such as the processing device 255 shown in FIG. 2D. Signals, including data and/or command signals, may be transmitted wirelessly between the retractor apparatus 200 and the processing device 255 using a suitable wireless communication protocol or standard (e.g., an IEEE 802.15x (BLUETOOTH) connection or IEEE 802.11 (WiFi) connection). In embodiments, command signals to energize particular electrodes 247 may be received wirelessly from a remote processing device 255. Alternately or in addition, the retractor apparatus 200 may include a user interface component (e.g., one or more buttons) that may be used to trigger the stimulation signals. When the user actuates the user interface component, a signal may be sent to the processing device 255 to enable the device 255 to synchronize the recording of the evoked EMG response(s) with the triggering of the stimulation signal(s).

Although the embodiment of FIG. 2D shows the power source 246 and circuitry 249 for generating stimulation signals located on the retractor apparatus 200, it will be understood that one or both of these components may be omitted from the retractor apparatus 200. For example, the retractor apparatus 200 and/or the individual retractor blades 227 may be connected to a separate neurophysiological monitoring device by a wire connection. In some embodiments, a neurophysiological monitoring device may include a handheld probe that may be selectively coupled to the retractor apparatus 200 or to individual retractor blades 227 to provide nerve stimulation signals. For example, a handheld probe may be inserted into the ports 241 as shown in FIG. 1.

In some embodiments, a connection 257 between the retractor apparatus 200 and the robotic arm 101 may be used for data/control signals and/or to provide power to the retractor apparatus 200, as is schematically illustrated in FIG. 2D. The connection 257 between the robotic arm 101 and retractor apparatus 200 may need to pass through a sterile barrier (e.g., a surgical drape) covering the arm 101 and may utilize a non-contact transmission mechanism, such as inductive or capacitive coupling and/or optical or other electromagnetic transmission methods.

Figure 3A:
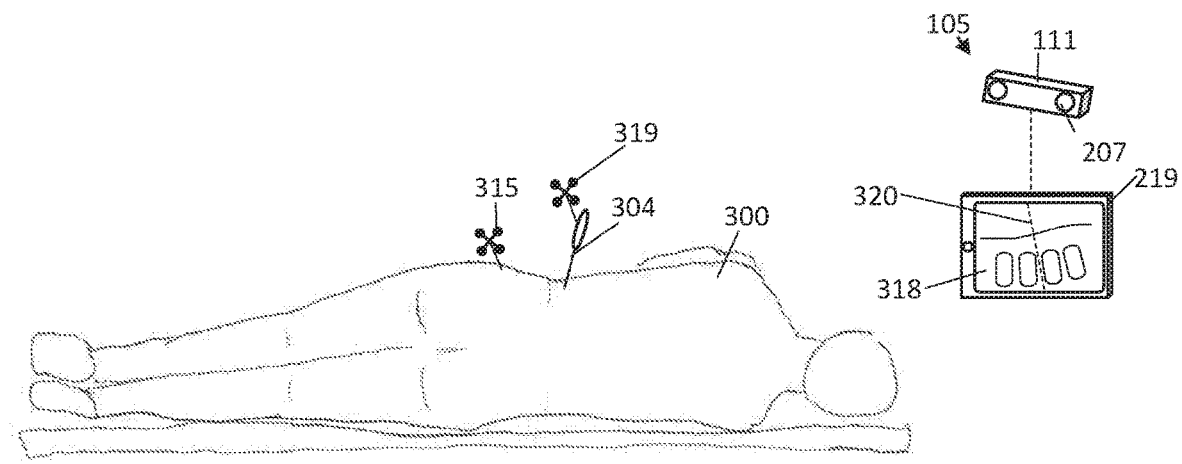
FIGS. 3A-3E schematically illustrate a robotic-assisted lateral access spine procedure performed on a patient.

FIGS. 3A-3E illustrate a method of performing a surgical procedure using a retractor apparatus 200 such as described above. The surgical procedure may be a robot-assisted spinal procedure, such as a minimally-invasive lateral transpsoas interbody fusion. In FIG. 3A, a tracked instrument 304 may be used to define and set a target trajectory or target location within the body of the patient 300. In embodiments, the instrument 304 may be a handheld instrument that may be gripped and easily manipulated by a user (e.g., a surgeon). The instrument 304 may be a handheld pointer or stylus device that may be manipulated by the surgeon to point to or touch various locations on the skin surface of the patient 300. Alternately, the instrument 304 may be an invasive surgical instrument (e.g., dilator, cannula, needle, scalpel, etc.) that may be inserted into the body of the patient. The instrument 304 may further include at least one marker device 319 to enable the instrument 304 to be tracked using a motion tracking system 105, as described above. In this embodiment, the at least one marker device 319 includes an array of reflective spheres that are rigidly fixed to the instrument 304, although other types of active or passive markers may be utilized. The marker device 319 may be in a known, fixed geometric relationship with the instrument 304 such that by tracking the marker device 319 the motion tracking system 105 may determine the position and/or orientation of the instrument 304. The motion tracking system 105 may also track the current position and orientation of the patient 300 via a reference marker device 315 which may be rigidly attached to the patient 300 (e.g., clamped or otherwise attached to a bony portion of the patient's anatomy). The motion tracking system 105 may thereby continuously track the position and/or orientation of the instrument 304 relative to the patient 300 (i.e., within a common, patient-centric coordinate system).

Patient images 318, which may have previously-been obtained by an imaging device 103 (see FIG. 1), may be registered to the common patient-centric coordinate system using an image registration technique, as described above. One or more patient images 318 may be shown on a display screen of a display device 219, as shown in FIG. 3A. The patient images 318 on the display device 219 may be augmented by one or more graphical elements indicating the current position/orientation of the instrument 304 within the patient-centric coordinate system. For example, as shown in FIG. 3A, a dashed line 320 superimposed over the patient image 318 may indicate the trajectory defined by an imaginary ray projected forward from the tip of the instrument 304. As the instrument 304 is moved relative to the patient 300, the location of the graphical element(s) 320 on the display screen may be updated to reflect the current pose of the instrument 304 relative to the patient.

In embodiments, the user (e.g., surgeon) may manipulate the instrument 304 while viewing the augmented patient images on the display device 219 to identify a desired trajectory though the patient 300 to a surgical area. For example, for a lateral transpoas interbody fusion, the surgeon may utilize the instrument 304 to identify a path through the patient's anatomy to the surgical site (e.g., an intervertebral disc requiring a surgical intervention). The path may be selected to minimize disturbance to other anatomic features, such as neural structures (e.g., lumbar nerve plexus) located around or within the psoas muscle. The user may set a particular trajectory using a user-input command (e.g., a button push, a voice command, etc.). The selected trajectory within the common coordinate system may be saved in a memory (e.g., in computer 113).

After a trajectory is set, the surgeon may make an incision 331 in the patient's skin surface and insert an invasive surgical instrument through the incision 331 and into the patient's body. The invasive surgical instrument may be, for example, a K-wire, a needle, an awl or the like that may be advanced along the pre-determined trajectory to the surgical site of interest. In some embodiments, the invasive surgical instrument may be a tracked instrument that is pre-calibrated and registered within the image guided surgery system. This may enable the motion tracking system 105 to track the advancement of the instrument within the patient 300. The display device 219 may graphically illustrate the position of the instrument as it is advanced along the pre-set trajectory.

In some embodiments, a robotic arm 101 such as shown in FIG. 1 may be used to guide the insertion of an invasive surgical instrument along the pre-determined trajectory. For example, the robotic arm 101 may be controlled to move the end effector 102 of the arm 101 into alignment with the pre-defined trajectory and/or over the pre-determined target location. The end effector 102 may include a guide mechanism (e.g., such as a hollow tube) aligned with the pre-set trajectory and through which the surgical instrument may be inserted to guide the instrument along the trajectory. Alternately, the invasive surgical instrument may be inserted by the surgeon using a free-hand technique (i.e., without robotic assistance). The insertion may be performed with or without the use of image guidance/surgical navigation.

The surgeon may also perform intraoperative neurophysiological monitoring (IONM) such as by inserting a handheld neuro-monitoring probe device into the incision site of the patient to electrically stimulate the surrounding tissue and detecting the evoked EMG response to detect for the presence of nerve(s). Alternately or in addition, the invasive surgical instrument (e.g., K-wire, needle, etc.) that is inserted into the patient's body may be equipped with IONM functionality (e.g., it may include one or more electrodes configured to stimulate the surrounding tissue). This may enable the surgeon to repeatedly monitor for nerves as the instrument is advanced to the target site (e.g., an intervertebral disc).

Figure 3B:
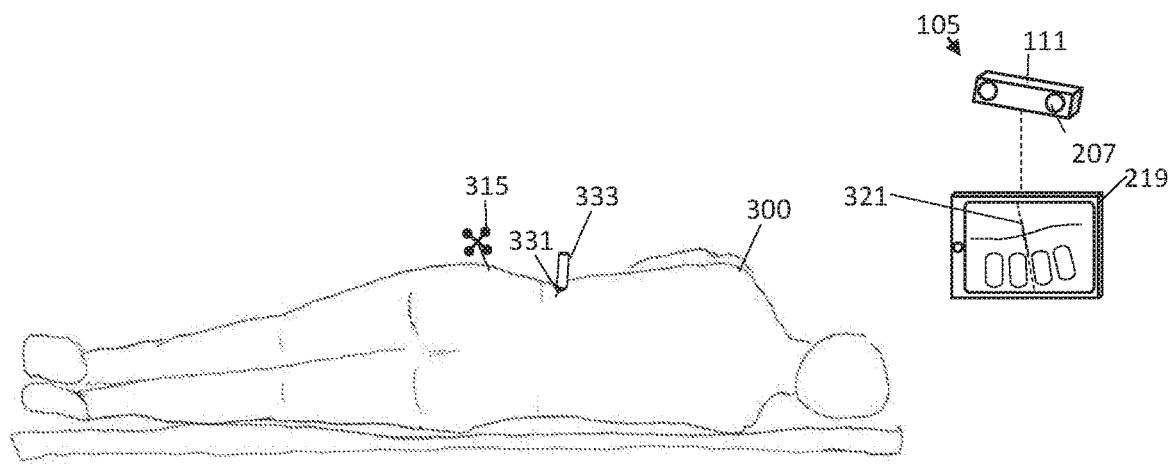

In embodiments, after the surgeon has advanced an initial surgical instrument along the trajectory to the surgical site, one or more additional instruments may be inserted to dilate the tissue between the incision and the surgical site. For example, a series of dilating cannulas may be inserted over the initial surgical instrument (e.g., a K-wire). FIG. 3B illustrates an outermost cannula 333 of a series of sequential dilating cannulas within the surgical opening 331. It will be understood that each of the dilating instruments (e.g., cannulas 333) may optionally be tracked by the motion tracking system 105. Also, each additional instrument inserted into the patient 300 may optionally include IONM functionality to detect nerve proximity during or after it's insertion into the patient 300.

Figure 3C:
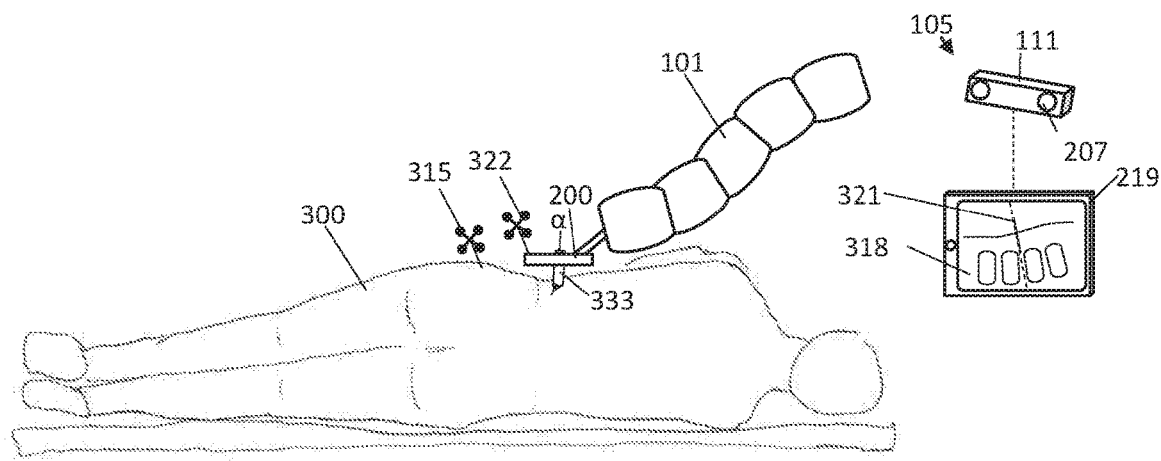

As shown in FIG. 3C, a robotic arm 101 having a retractor apparatus 200 attached thereto may be controlled to move the retractor apparatus 200 over the surgical site. In embodiments where a robotic arm 101 is used to guide the insertion of a K-wire or other instrument down to the surgical site, the end effector 102 used for guiding may be removed from the robotic arm 101 and a retractor apparatus 200 such as shown in FIGS. 2A-2E may be attached to the end of the arm 101 (e.g., using a quick connect/disconnect attachment mechanism). The retractor apparatus 200 may be pre-calibrated and registered within the image guided surgery system and may include a marker device 322 to enable the position of the retractor apparatus 200 to be tracked and optionally shown on the display device 219. The retractor apparatus 200 may be moved by the robotic arm 101 into a position such that a retractor axis, a, extending through the central open region 225 of the apparatus 200 may be aligned (i.e., collinear) with the pre-set trajectory into the patient 300. The retractor axis a may extend down the center of the working channel 237 of the retractor apparatus 200 when the retractor blades 227 are attached. In embodiments, a controller for the robotic arm 101 may move the retractor apparatus 200 autonomously to align the retractor apparatus with the pre-set patient trajectory. Alternately, the robotic arm 101 may be manually moved using a hand guiding mode to align the retractor apparatus over the pre-set trajectory.

The retractor blades 227 may be attached to the frame 221 of the retractor apparatus 200 (see FIGS. 2A-2E). In one embodiment, the diameter of the working channel 237 of the retractor apparatus in an initial configuration (i.e., $D_1$ in FIG. 2A) may be approximately equal to the outer diameter of the tissue dilator 333. The retractor blades 227 may be inserted through the respective guides 229 of the retractor assembly 200 and advanced along the outer surface of the dilator 333 into the patient 300. In embodiments, the outer surface of the dilator 333 may include slots or similar features configured to guide the retractor blades 227 along the dilator 333 and into the surgical opening. After the retractor blades 227 are inserted into the patient 300, the dilator 333 may be withdrawn from the patient 300 through the central open region 225 of the retractor apparatus 200 to expose the working channel 237 that may extend to the surgical site.

In an alternative embodiment, the retractor blades 227 may first be inserted into the patient 300 (e.g., over the outer surface of the dilator 333) and may then be attached to the frame 221 of the retractor assembly 200 via a coupling mechanism. The coupling mechanism may attach the distal ends of the actuators 233 to the retractor blades 227. The coupling mechanism may be a latch (e.g., a mechanical or electromagnetic-based latch), a mechanical fastener, a clamp, a clip and/or mating features on the actuator 233 and the blade 227 that enable the blade 227 to be secured to the actuator 233. In one example, the mating features may include a protrusion on the outer surface of the blade 227 that slides into a corresponding slot in the actuator 233 (e.g., to provide a dovetail or bayonet-type connection). Alternately, a protrusion on the actuator 233 may slide into a slot on the blade 227. In embodiments, the retractor blades 227 may be secured to the frame 221 of the retractor apparatus 200 by rotating the blades in a first direction with respect to the frame 221. The blades 227 may be detached from the frame 221 by rotating the blades 227 in the opposite direction.

In other alternative embodiments, the surgeon may create a pathway through the patient's anatomy to the surgical site with or without the use of an image guided surgery system. For example, the surgeon may optionally utilize image guidance/surgical navigation to pre-plan an initial path to the surgical site, and may then use a manual (i.e., non-navigated) approach for deep tissue dissection and/or cannulation. One or more invasive surgical instruments inserted into the patient (e.g., a K-wire, a needle, a cannula, etc.) may be tracked by the motion tracking system 105 (either directly by attaching a marker 319 to the invasive instrument, or indirectly by touching or aligning a tracked handheld probe 304 to the invasive instrument) to determine the actual trajectory of the instrument(s) (e.g., cannula 333) within the patient in the common coordinate system. The retractor apparatus 200 may then be moved by the robotic arm 101 to align the retractor axis, α, with the instrument trajectory, as described above.

In various embodiments, the retractor blades 227 may be used for performing IONM of the patient 300 as discussed above at any time before, during and/or after the blades 227 are attached to the frame 221 of the retractor apparatus 200.

Figure 3D:
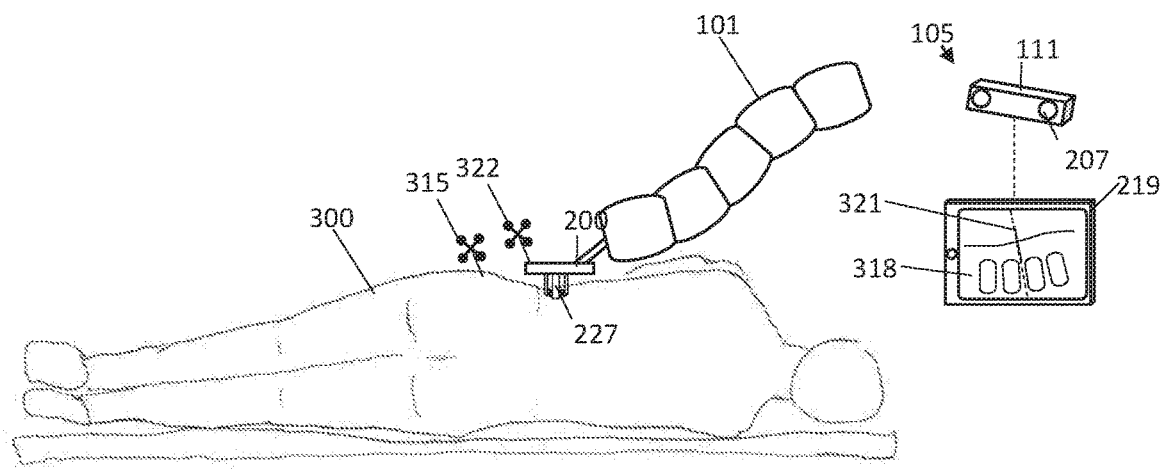
Figure 3E:
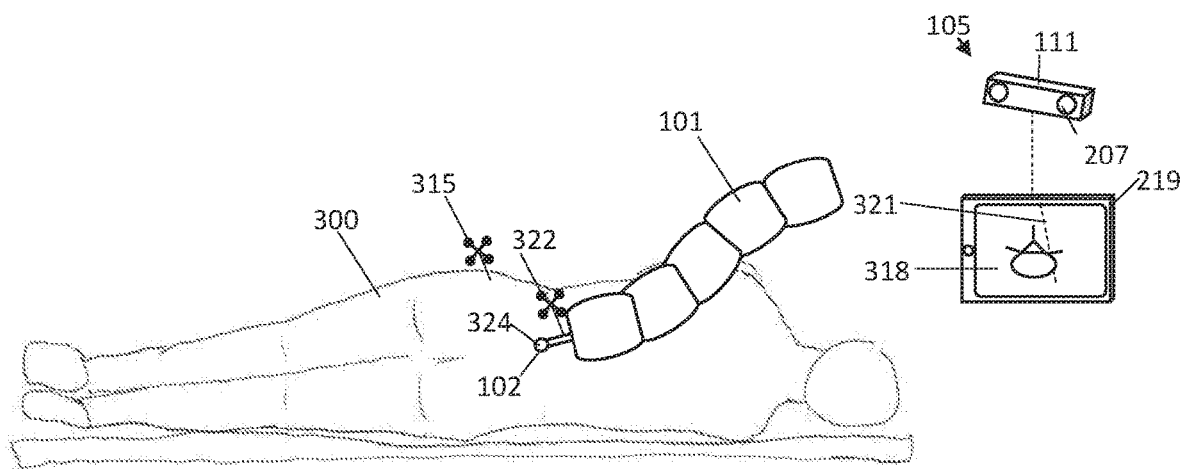

After the retractor blades 227 are attached to the frame 221, the blades 227 may be retracted to increase the size of the working channel 237, as shown in FIG. 3D. In embodiments, feedback data (e.g., encoder data) from the retractor apparatus 200 may be provided to the image guided surgery system to enable patient images shown on the display device 219 to be augmented by a graphical indication of real-time positions of the blades 227 and/or the size of the working channel 237 within the patient 300.

During a surgical procedure, the robotic arm 101 may maintain the position of the retractor apparatus 200 relative to the patient 300. In embodiments, the robotic arm 101 may be configured to compensate for any patient movement to maintain the working channel 237 aligned along the pre-set trajectory. The surgeon may perform a surgical procedure, such as in interbody fusion, through the working channel 237 defined by the retractor apparatus 200. In particular, disc material or other pathologic tissue may be removed and an implant (e.g., a spacer or cage) may be inserted through the working channel 237 and placed in the intervertebral space. IONM may be utilized as desired to minimize damage or irritation to surrounding neural structures.

After the insertion of an implant, the retractor apparatus 200 may be removed from the patient 300 and the incision may be closed. The patient 300 may optionally be scanned using an imaging device 103 such as shown in FIG. 1 to confirm the placement of the implant. The procedure may also include the insertion of stabilization elements (e.g., a rod and screw system) to stabilize the spine and allow the adjacent vertebra to properly fuse in the case of a fusion procedure. In some embodiments, the placement of screws (e.g., pedicle screws) may be performed using the robotic arm 101 and/or image guided surgery system without requiring the patient 300 to be repositioned or moved. In particular, patient images 318 on the display device 219 may be used by the surgeon to set one or more trajectories 323 for screw placement (e.g., via a posterior or anterior approach of the patient 300 lying on his/her side). The robotic arm 101 may be moved into position to align the end effector 102 over the pre-set trajectory. The retractor apparatus 200 may be removed and replaced on the robotic arm 101 by an end effector 102 that includes a guide mechanism (e.g., hollow tube 324) through which surgical instruments may be inserted along the pre-set trajectory. Various instruments, such as one or more cannulas, a drill, a screw and a screw driver, may be inserted through the end effector 102 and to place the screw in the patient.

Figure 4A:
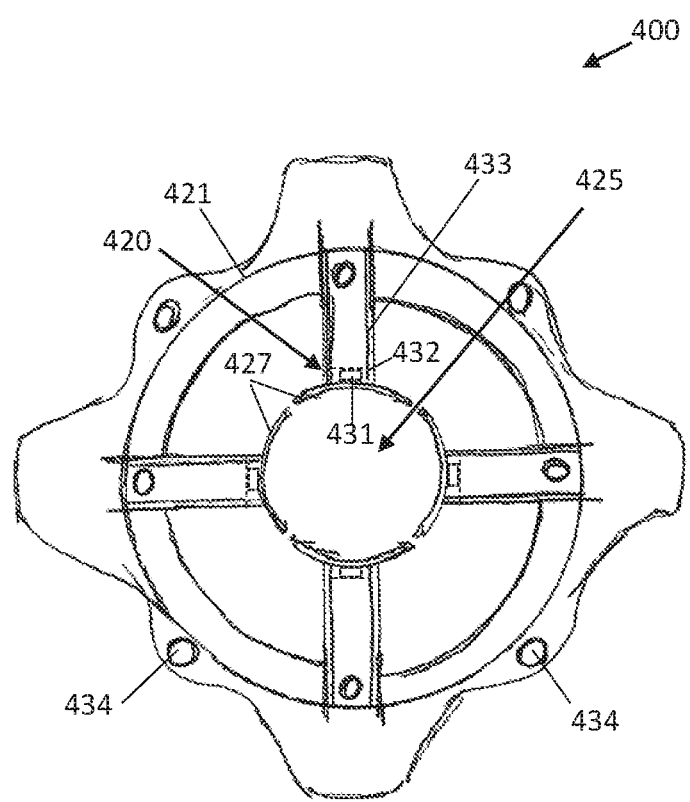
FIGS. 4A-4B illustrate a further embodiment retractor apparatus.
Figure 4B:
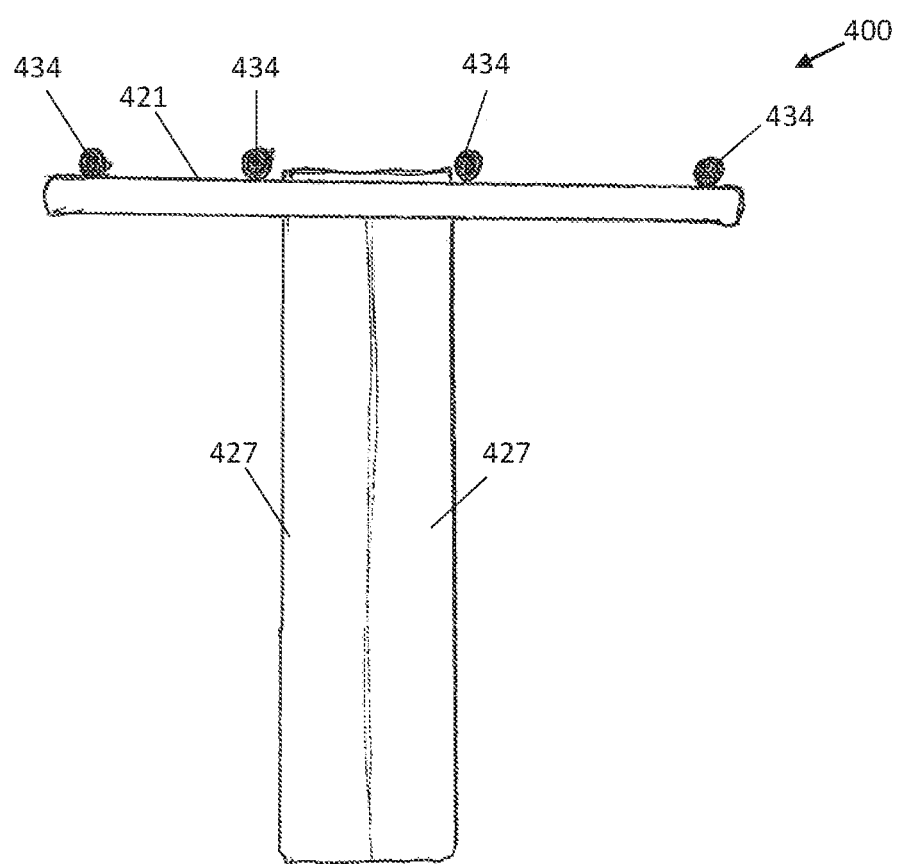

FIGS. 4A-4B illustrate an alternative embodiment of a retractor apparatus 400. The retractor apparatus 400 may be similar to retractor apparatus 200 shown in FIGS. 2A-2E. The retractor apparatus 400 includes a frame 421 having a central open region 425 as shown in the overhead view of FIG. 4A. The frame 421 may be coupled to a rigid support arm, such as robotic arm 101 shown in FIG. 1. In the embodiment of FIGS. 4A-4B, the frame 421 has a generally circular shape. The retractor apparatus 400 includes a plurality of actuators 433 extending into the central open region 425. The actuators 433 may each be independently extended and retracted within the central open region 425 using control features (e.g., sockets 435).

The retractor apparatus 400 includes a coupling mechanism 420 for mechanically coupling the actuators 433 to a plurality of retractor blades 427. In this embodiment, the coupling mechanism 430 comprises a projection 431 extending from the side of the retractor blade 427 that is received within a slot 432 in the actuator 433 to attach the retractor blade 427 to the actuator 433.

The retractor apparatus 400 may also include a plurality of markers 434 (e.g., reflective spheres) attached to apparatus, such as on the rigid frame 421 of the apparatus 400. A plurality of markers 434 (reflective spheres) are visible in the side view of the retractor apparatus 400 of FIG. 4B. The markers 434 may enable the retractor apparatus 400 to be tracked by a motion tracking system 105 as described above.

Figure 5:
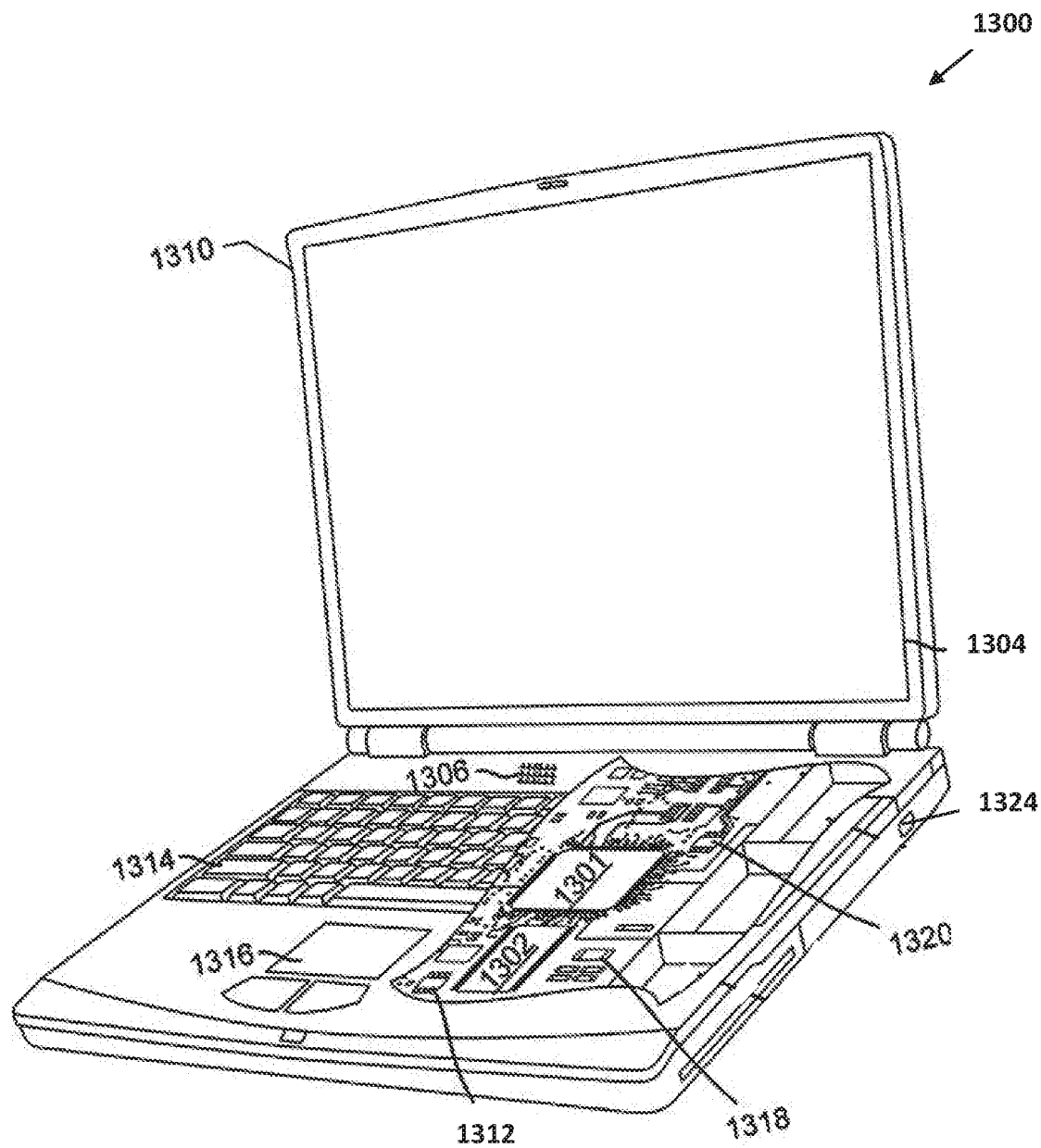
FIG. 5 schematically illustrates a computing device which may be used for performing various embodiments.

FIG. 5 is a system block diagram of a computing device 1300 useful for performing and implementing the various embodiments described above. While the computing device 1300 is illustrated as a laptop computer, a computing device providing the functional capabilities of the computer device 1300 may be implemented as a workstation computer, an embedded computer, a desktop computer, a server computer or a handheld computer (e.g., tablet, a smartphone, etc.). A typical computing device 1300 may include a processor 1301 coupled to an electronic display 1304, a speaker 1306 and a memory 1302, which may be a volatile memory as well as a nonvolatile memory (e.g., a disk drive). When implemented as a laptop computer or desktop computer, the computing device 1300 may also include a floppy disc drive, compact disc (CD) or DVD disc drive coupled to the processor 1301. The computing device 1300 may include an antenna 1310, a multimedia receiver 1312, a transceiver 1318 and/or communications circuitry coupled to the processor 1301 for sending and receiving electromagnetic radiation, connecting to a wireless data link, and receiving data. Additionally, the computing device 1300 may include network access ports 1324 coupled to the processor 1301 for establishing data connections with a network (e.g., LAN coupled to a service provider network, etc.). A laptop computer or desktop computer 1300 typically also includes a keyboard 1314 and a mouse pad 1316 for receiving user inputs.

The foregoing method descriptions are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not necessarily intended to limit the order of the steps; these words may be used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The hardware used to implement the various illustrative logics, logical blocks, modules, and circuits described in connection with the aspects disclosed herein may be implemented or performed with a general purpose processor, a graphics processing unit (GPU), a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored on as one or more instructions or code on a non-transitory computer-readable medium. The steps of a method or algorithm disclosed herein may be embodied in a processor-executable software module executed which may reside on a non-transitory computer-readable medium. Non-transitory computer-readable media includes computer storage media that facilitates transfer of a computer program from one place to another. A storage media may be any available media that may be accessed by a computer. By way of example, and not limitation, such non-transitory computer-readable storage media may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of non-transitory computer-readable storage media. Additionally, the operations of a method or algorithm may reside as one or any combination or set of codes and/or instructions on a machine readable medium and/or computer-readable medium, which may be incorporated into a computer program product.

The preceding description of the disclosed aspects is provided to enable any person skilled in the art to make or use the present invention. Various modifications to these aspects will be readily apparent to those skilled in the art, and the generic principles defined herein may be applied to other aspects without departing from the scope of the invention. Thus, the present invention is not intended to be limited to the aspects shown herein but is to be accorded the widest scope consistent with the principles and novel features disclosed herein.

What is claimed is:

1. A surgical robotic system, comprising:
   a motion tracking system to track the position and orientation of one or more objects within a coordinate system;
   an imaging device comprising an o-shaped gantry to obtain image data of a patient positioned therein;
   a robotic arm defining an end movable relative to a support structure arranged adjacent to the o-shaped gantry of the imaging device, the support structure including a curved rail operatively attached to the o-shaped gantry of the imaging device, with the robotic arm defining a second end operatively attached to the curved rail, with a position of the second end of the robotic arm being adjustable along the curved rail, and with the robotic arm configured to maintain alignment of the end relative to a target position of a patient's body defined within the coordinate system; and a retractor apparatus attached to the robotic arm, the retractor apparatus comprising:
      a frame attached to the robotic arm, the frame defining a central open region;
      a connecting member that connects the frame to the end of the robotic arm for concurrent movement relative to the support structure;
      a plurality of retractor blades;
      a plurality of coupling mechanisms for attaching the retractor blades within the central open region of the frame such that the retractor blades define a working channel interior of the retractor blades;
      a plurality of actuators extending between the frame and each of the coupling mechanisms and configured to move the retractor blades with respect to the frame to vary a dimension of the working channel; and
      a marker device fixed to the frame that enables the retractor apparatus to be tracked using the motion tracking system to track the position and orientation of the retractor apparatus within the coordinate system.

2. The surgical robotic system of claim 1, wherein the plurality of actuators are configured to move each retractor blade independently of movement of other retractor blades.

3. The surgical robotic system of claim 1, wherein the plurality of actuators are configured to extend and retract the retractor blades relative to the frame.

4. The surgical robotic system of claim 3, wherein the plurality of actuators are further configured to pivot the retractor blades relative to the frame.

5. The surgical robotic system of claim 1, wherein the plurality of actuators are manually operated to move the retractor blades.

6. The surgical robotic system of claim 1, wherein the plurality of actuators are driven by one or more motors attached to the frame.

7. The surgical robotic system of claim 1, wherein the marker device comprises an array of reflective spheres mounted to the frame.

8. The surgical robotic system of claim 1, wherein the frame includes one or more rails extending on the periphery of the central open region that are configured to enable surgical tools or instruments to be attached to the rail.

9. The surgical robotic system of claim 1, wherein at least one retractor blade comprises one or more channels extending through the at least one retractor blade.

10. The surgical robotic system of claim 1, wherein at least one retractor blade comprises an electrode on the at least one retractor blade for electrically stimulating surrounding tissue when the at least one retractor blade is inserted into a patient.

11. The surgical robotic system of claim 10, wherein the at least one retractor blade further comprises a conductive path extending on or within the at least one retractor blade for electrically coupling the electrode to a power source and a circuit for generating intraoperative neurophysiological monitoring (IONM) stimulation signals.

12. The surgical robotic system of claim 11, wherein at least one of the coupling mechanism and the at least one retractor blade includes a port for electrically connecting the electrode on the at least one retractor blade to a separate IONM probe device.

13. The surgical robotic system of claim 11, wherein at least one of the power source and the circuit for generating IONM stimulation signals is located on the frame of the retractor apparatus.

14. The surgical robotic system of claim 11, wherein at least one of electrical power and signals are transmitted from the robotic arm to the retractor apparatus.

15. The surgical robotic system of claim 1, wherein the plurality of coupling mechanisms for attaching the retractor blades comprise a plurality of guides through which the retractor blades are inserted.

16. The surgical robotic system of claim 1, wherein the tracking system includes an optical sensing device to track the position and orientation of the marker device and the robotic arm within the coordinate system.

17. The surgical robotic system of claim 15, wherein the plurality of guides are shaped to receive the retractor blades in a direction extending into the central open region defined by the frame.

18. The surgical robotic system of claim 1, wherein the connecting member is releasably attachable to the end of the robotic arm.

\* \* \* \* \*